United States Patent [19]

Kozikowski et al.

[11] Patent Number: 5,132,313

[45] Date of Patent: Jul. 21, 1992

[54] NON-COMPETITIVE NMDA RECEPTOR ANTAGONISTS AND METHODS FOR THEIR USE

[75] Inventors: Alan P. Kozikowski; Yuan-Ping Pang, both of Pittsburgh, Pa.

[73] Assignee: University of Pittsburgh, Pittsburgh, Pa.

[21] Appl. No.: 427,262

[22] Filed: Oct. 26, 1989

[51] Int. Cl.$^5$ .................. A61K 31/445; C07D 211/14
[52] U.S. Cl. ..................................... 514/325; 514/429; 546/203; 546/204; 548/529; 558/17; 564/308
[58] Field of Search ................ 546/203, 204; 548/529; 514/325, 429; 558/17; 564/308

[56] References Cited

U.S. PATENT DOCUMENTS

| | | | |
|---|---|---|---|
| 3,111,527 | 11/1963 | Godefroi | 549/43 |
| 3,206,480 | 9/1965 | Godefroi | 549/460 |
| 4,837,226 | 6/1989 | Coughenour | 514/443 |

OTHER PUBLICATIONS

Godefroi, et al., Journal of Organic Chemistry, 28:1112–1119 (1963).

Primary Examiner—Joseph P. Brust
Assistant Examiner—Jacqueline Haley
Attorney, Agent, or Firm—Pennie & Edmonds

[57] ABSTRACT

The present invention relates to novel NMDA receptor antagonists and methods for their use. The present invention also provided pharmaceutical compositions comprising such NMDA receptor antagonists.

16 Claims, No Drawings

NON-COMPETITIVE NMDA RECEPTOR ANTAGONISTS AND METHODS FOR THEIR USE

This invention was made with government support under Grant No. 5 R01 DA05587 awarded by the National Institutes of Health, National Institute on Drug Abuse. The government has certain rights in this invention.

TABLE OF CONTENTS

TECHNICAL FIELD
BACKGROUND OF THE INVENTION
SUMMARY OF THE INVENTION
DETAILED DESCRIPTION OF THE INVENTION
EXAMPLES
  EXAMPLE I — SYNTHESIS OF UNSUBSTITUTED FLUORENAMINES ($X_1=X_2=H$)
  EXAMPLE II — SYNTHESIS OF $X_1/X_2$ SUBSTITUTED FLUORENAMINES

TECHNICAL FIELD

The present invention relates to novel NMDA receptor antagonists and methods for their use. The present invention also provides pharmaceutical compositions comprising such NMDA receptor antagonists.

BACKGROUND OF THE INVENTION

N-methyl-D-aspartate (NMDA) receptors are prevalent in the brain and are activated by excitatory amino acids, e.g. glutamate and aspartate.

Several non-competitive NMDA receptor antagonists are known. (A non-competitive receptor antagonist is a compound that decreases the potency of an agonist, but whose antagonism cannot be overcome entirely by increasing agonist dosage.) Examples of non-competitive NMDA receptor antagonists are phencyclidine, which is commonly referred to as "PCP" or "angel dust," the PCP analog 1-[1-(2-thienyl)-cyclohexyl]-piperidine, which is commonly referred to as "TCP", and the compound 5-methyl-10,11-dihydro-5H-dibenzo [a,d] cycloheptene-5,10-imine, which is commonly referred to as "MK-801"; see U.S. Pat. No. 4,399,141.

Non-competitive NMDA receptor antagonists are useful for treating or preventing neuronal cell loss associated with stroke, ischemia, CNS trauma, hypoxia and hypoglycemia, as well as neurodegenerative diseases including Alzheimer's disease, amyotrophic lateral sclerosis, Huntington's disease and Down's syndrome. See J. A. Kemp et al., *Non-competitive Antagonists of Excitatory Amino Acid Receptors*, TINS, Vol. 10, No. 7, 294-298 (1987).

SUMMARY OF THE INVENTION

The present invention provides compounds represented by the general formula I:

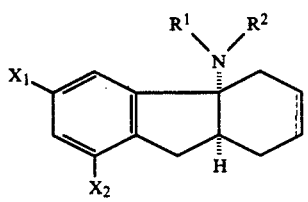

wherein:
  $X_1$ is selected from the group consisting of H, OH, $NH_2$, SH, N=C=S and $OCH_3$;
  $X_2$ is selected from the group consisting of H, OH, $NH_2$, SH, N=C=S and $OCH_3$;
  $R^1$ is selected from the group consisting of H and a $C_1$-$C_4$ linear or branched alkyl group;
  $R^2$ is selected from the group consisting of H and a $C_1$-$C_4$ linear or branched alkyl group;
  and $R^1$ and $R^2$ can be joined to form a pyrrolidine ring or a piperidine ring;
  ⎓ represents a saturated or unsaturated bond; and pharmaceutically acceptable salts thereof;
with the proviso that:
  (1) said compound is in the cis-fused form; and
  (2) said compound is the enantiomer of R stereochemistry at the amine bearing carbon atom substantially free of any other stereoisomer.

The present invention also provides a method for treating or preventing neuronal cell loss, treating neurodegenerative diseases or ameliorating the neurotoxic effect induced by excitatory amino acids interacting with the NMDA receptor of a nerve cell in a mammal which comprises administering to said mammal a therapeutically effective amount of a compound represented by general formula I.

The present invention also provides a method for blocking ion fluxes through the NMDA receptor-associated ion channel in a mammal which comprises administering to said mammal an effective amount of a compound represented by general formula I.

DETAILED DESCRIPTION OF THE INVENTION

The present invention provides compounds represented by the general formula I:

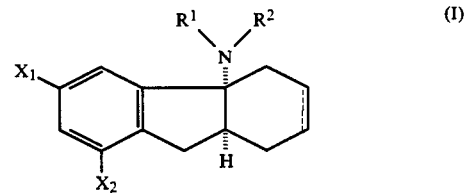

wherein:
  $X_1$ is selected from the group consisting of H, OH, $NH_2$, SH, N=C=S and $OCH_3$;
  $X_2$ is selected from the group consisting of H, OH, $NH_2$, SH, N=C=S and $OCH_3$;
  $R^1$ is selected from the group consisting of H and a $C_1$-$C_4$ linear or branched alkyl group;
  $R^2$ is selected from the group consisting of H and a $C_1$-$C_4$ linear or branched alkyl group;
  and $R^1$ and $R^2$ can be joined to form a pyrrolidine ring or a piperidine ring;
  ⎓ represents a saturated or unsaturated bond; and pharmaceutically acceptable salts thereof;
with the proviso that:
  (1) said compound is in the cis-fused form; and
  (2) said compound is the enantiomer of R stereochemistry at the amine bearing carbon atom substantially free of any other stereoisomer.

For the purpose of the subject invention, the term "substantially free of an other stereoisomer" means that the composition contains no more than about 10% of the enantiomer of S stereochemistry at the amine bearing carbon atom.

The compounds represented by general formula I are non-competitive NMDA receptor antagonists. The compounds represented by general formula I bind to the same receptor site as the non-competitive NMDA receptor antagonists PCP, TCP and MK-801. It has also been observed that the compounds of general formula I block the ion fluxes, e.g. calcium entry, through the NMDA receptor-associated ion channel. Thus, the compounds represented by general formula I can be utilized to treat conditions wherein overstimulation of the NMDA receptors takes place, which results in excessive influx of ions, e.g. calcium, through the NMDA receptor-associated ion channels.

The ability of the compounds represented by formula I to be NMDA receptor antagonists renders these compounds useful as pharmaceutical agents. These compounds will be useful for treating or preventing neuronal cell loss associated with stroke, ischemia, CNS trauma, hypoxia, and hypoglycemia, as well as neurodegenerative diseases including Alzheimer's disease, amyotrophic lateral sclerosis, Huntington's disease and Down's syndrome.

The compounds represented by formula I are also useful for ameliorating the neurotoxic effect induced by excitatory amino acids interacting with the NMDA receptor of a nerve cell. Such neurotoxic effects may be caused by ischemic brain insults, which cause release of endogenous glutamate. The compounds represented by formula I can be administered prophylatically, for example, before a surgical procedure or other treatment that may be expected to cause reduced blood flow to the brain or spinal cord, thereby, ameliorating neurodegradation. Such compounds also can be administered after trauma, for example, to the head or spinal cord to ameliorate the resulting neurodegeneration that may result therefrom.

The compounds represented by general formula I can be administered to a mammal, e.g. human subject, either alone or, preferably, in combination with pharmaceutically acceptable carriers, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a compound represented by general formula I, such compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparations isotonic.

When a compound represented by general general formula I is used as in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.01 mg/kg to about 500 mg/kg of body weight on a regimen of 1-4 times per day, and preferably, of from about 0.01 mg/kg to about 25 mg/kg of body weight on a regimen of 1 to 4 times per day. In some cases, however, it may be necessary to use dosages outside these limits.

EXAMPLES

EXAMPLE I

Synthesis of Unsubstituted Fluorenamines ($X_1=X_2=H$)

This example describes the synthesis of the compounds represented by general formula I wherein $X_1=X_2=H$; $R^1=H$, ethyl; $R^2=H$; and ⸺ is saturated, unsaturated. Also, this example describes the synthesis of the compounds represented by general formula I wherein $X_1=X_2H$; $R^1=H$, ethyl; $R^2=H$; and ⸺ is saturated, unsaturated, however, the compounds are the enantiomer of S stereochemistry at the amine bearing carbon atom and, therefore, are outside the scope of the subject invention.

Also, it should be noted that the numbers following the named compounds in EXAMPLE I correspond to the numbered compounds of Scheme 1.

General Procedures

Tetrahydrofuran and ethyl ether were distilled from sodium benzophenone ketyl prior to use. Benzene and toluene were distilled from $CaH_2$ prior to use. Methylene chloride was dried by passage through a column of activity I neutral alumina and stored over 4-Å molecular sieves. Solvents used for chromatography were purchased in 5-gal drums, redistilled from an all-glass apparatus, and stored in glass bottles. Silica gel 60 (Merck, 70-230 mesh ASTM or 230-400 mesh ASTM for flash chromatography) was used for column chromatography. TLC was performed on Merck Silica Gel 60F-254 (0.25 mm, precoated on glass). Other reagents were used as supplied by the Aldrich Chemical Company in Milwaukee, Wis. or the Sigma Chemical Company in St. Louis, Mo. or purified as noted.

Melting points were determined in open capillary tubes on a Thomas-Hoover capillary melting point apparatus and are uncorrected. Infrared spectra were recorded on a Mattson CYGNUS 100 spectrophotometer. $^1H$ NMR spectra were taken on a Bruker AF-300 (300 MHz) or Bruker AM-500 (500 MHz) instruments in $CDCl_3$ or in the solvent noted. $^{13}C$ NMR spectra were taken on a Bruker AM-500 (125.76 MHz) instrument in $CDCl_3$. Chemical shifts are reported in δ units with reference to $Me_4Si$ ($\beta=0.00$ ppm) or $CDCl_3$ ($\delta=7.26$ ppm) as internal standards. Mass spectra were obtained on a Varian MAT CH 5 and VG 70-G instruments. Optical rotations were measured on a Perkin-Elmer 241 Polarimeter using a standard cell.

Indene-3-carboxylic Acid (II)

To a stirred solution of indene (21.9 mL, 188 mmol) in 150 mL of dry ethyl ether was added 129 mL (200 mmol) of η-BuLi dropwise at room temperature over 30 minutes with the evolution of butane. The rust colored mixture was refluxed for 2 h, and then poured in a thin stream onto 40 g of Dry Ice. The mixture was shaken at room temperature for 2 h, after which time 1 L of H$_2$O was cautiously added. The aqueous layer was acidified with 10% HCl and then extracted with ethyl ether. Recrystallization from benzene gave 20 g (80%) of indene-3-carboxylic acid as yellowish crystals.

mp 159–160° C.;

Ir (KBr) $\nu$ 3050, 2957, 2903, 2881, 2774, 2718, 2658, 2592, 1682, 1559, 1460, 1418, 1254, 899, 760, 721, 702 cm$^{-1}$;

$^1$H NMR (CDCl$_3$, 300 MHz) $\delta$ 8.09 (1H, d, J=6.0 Hz), 7.66 (1H, t, J=1.8 Hz), 7.51 (1H, d, J=7.3 Hz), 7.39 (1H, t, J=7.1 Hz), 7.30 (1H, dd, J$_1$=0.9 Hz, J$_2$=7.62 Hz), 3.59 (2H, d, J=1.3 Hz);

MS (70 eV), m/z 160 (M+), 132, 115, 89, 63;

HRMS calcd for C$_{10}$H$_8$O$_2$ 160.0524, found 160.0524.

1,4,4a,9a-Tetrahydro-4a-fluorenecarboxylic Acid (III)

6.7 g (41.8 mmol) of indene-3-carboxylic acid in 15 mL of toluene containing a trace of t-butylcatechol was heated to 120° C. with 14 mL (168 mmol) of 1,3-butadiene for 24 hours in a 650 mL Parr pressure reaction bomb. Cooling of the vessel caused part of the product to crystallize out of the reaction mixture. The crystalline product, reaction mixture, and part of the adhering polymeric material were dissolved in boiling isooctane. The suspension was filtrated through Celite. Refrigeration of the filtrate deposited 8.5 g (95%) of the adduct III as white crystals:

mp 117–118° C.;

IR (CHCl$_3$) $\nu$ 3027, 2936, 2902, 1694, 740 cm$^{-1}$;

$^1$H NMR (CDCl$_3$, 300 MHz) $\delta$ 11.90–10.80 (1H, br s), 7.3–7.31 (1H, m), 7.25–7.13 (3H, m), 5.85–5.73 (2H, m), 3.18–3.04 (2H, m), 2.90–2.79 (1H, m), 2.75–2.61 (1H, m), 2.56–2.42 (1H, m), 2.19–2.01 (2H, m);

MS (70 eV), m/z 214 (M+), 160, 141, 128, 116, 91, 77, 57;

HRMS calcd for C$_{14}$H$_{14}$O$_2$ 214.0994, found 214.0994.

1,4,4a,9a-Tetrahydro-4a-fluorenecarboxylic Acid Amide (IV)

A solution of 5.8 g (27.1 mmol) of the adduct III in 25 mL of benzene containing 6 mL (82.26 mmol) of freshly distilled thionyl chloride was refluxed under nitrogen for 2h. The cooled mixture was then added slowly to vigorously stirred, concentrated ammonium hydroxide (100 mL) at 0°–5° C. under nitrogen. After addition was completed, the resulting mixture was stirred for 1 h at 0° C. Separation of the phases, and washing of the organic phase with 1N NaOH followed by drying and stripping of solvent gave the crude solid amide. Recrystallization from isooctane afforded 6 g (100%) of the amide IV as white crystals:

mp 79.5°–81° C.;

IR (CHCl$_3$) $\nu$ 3479, 3340, 3025, 2902, 1668, 760, 740 cm$^{-1}$;

$^1$H NMR (CDCl$_3$, 300 MHz) $\delta$ 7.30–7.17 (4H, M), 6.93–5.38 (2H br, d), 5.92–5.47 (2H, m), 3.08 (1H, dd, J$_1$=7.0 Hz, J$_2$=15.2 Hz), 2.94–2.76 (2H, m), 2.66 (1H, dd, J$_1$=6.9 Hz, J$_2$=15.2 Hz), 2.47–2.34 (1H, m), 2.26–2.14 (1H, m) 2.03–1.90 (1H, m), MS (70 eV), m/z 213 (M+), 169, 154, 141, 128, 115, 91;

HRMS calcd for C$_{14}$H$_{15}$ON 213.1154, found 213.1154.

1,4,4a,9a-Tetrahydro-4a-fluorenecarbamic Acid Methyl Ester (V)

To a sodium methoxide solution, freshly prepared from 1 g (43.5 mmol) of sodium in 37 mL of dry methanol was added 2 g (9.39 mmol) of the amide IV at room temperature. The mixture was cooled to −20° C., at which stage 0.5 mL (19.41 mmol) of Br$_2$ was introduced slowly at −20° C. Upon completion the solution was allowed to warm to room temperature, and then refluxed for 1.5 h. Acetic acid (1.7 mL, 29.7 mmol) was added to the cooled solution. The solution was concentrated under reduced pressure, and the residue, suspended in ethyl ether, was washed with H$_2$ and saturated aqueous NaCl and dried over MgSO$_4$. Column chromatography on silica with 50% EtOAc in hexane as eluent afforded 1.9 g (88%) of the carbamate as a yellowish oil:

R$_f$=0.58 (50% EtOAc in hexane);

IR (CHCl$_3$) $\nu$ 3327, 3021, 2940, 2895, 2832, 1702, 1494, 1250, 744, 717 cm$^{-1}$;

$^1$H NMR (CDCl$_3$, 300 MHz) $\delta$ 7.28–7.14 (4H, m), 5.86–5.64 (2H, m), 4.90 (1H, br s), 3.59 (3H, s), 3.08 (2H, dd, J$_1$=6.0 Hz, J$_2$=18 Hz), 2.62–2.41 (3H, m), 2.37–2.26 (1H, m), 2.10–2.00 (1H, m);

MS (70 eV), m/z 243 (M+), 211, 202, 189, 168, 157, 141, 130, 115, 103, 77, 55;

HRMS calcd for C$_{15}$H$_{17}$NO$_2$ 243.1259, found 243.1260.

1,4,4a,9a-Tetrahydro-4a-fluorenamine (VI)

A solution of 2.0 g (8.23 mmol) of the carbamate in 24 mL of diethylene glycol was refluxed with 100 mL of 24% aqueous KOH for 30 h. The reaction mixture was extracted with ethyl ether. The extract was concentrated under reduced pressure and then added to 100 mL of 5% HCl. The aqueous solution was washed with methylene chloride, its pH was adjusted to 12 with 5 N NaOH, and then the solution was extracted with methylene chloride. Evaporation of the extract afforded 1.2 g (80%) of the amine as white crystals.

R$_f$=0.27 (40% EtOAC in hexane, silica TLC saturated with NH$_3$);

IR (CHCl$_3$) $\nu$ 3345, 3273, 3021, 2898, 1458, 758, 730 cm$^{-1}$;

$^1$H NMR (CDCl$_3$, 300 MHz) $\delta$ 7.32–7.29 (1H, m), 7.26–7.15 (3H, m), 5.81–5.69 (2H, m), 2.94 (1H, dd, J$_1$=7.3, J$_2$=15.1), 2.62–2.48 (2H, m), 2.32–2.22 (1H, m), 2.19–2.10 (3H, m), 1.64 (2H, s);

$^{13}$C NMR (CDCl$_3$, 125.76 MHz) $\delta$ 152.57, 140.98, 126.68, 126.39, 125.09, 125.04, 124.99, 121.11, 60.06, 47.40, 36.55, 35.47, 25.46;

MS (70 eV), m/z 185 (M+), 182, 165, 156, 152, 149, 144, 141, 131;

HRMS calcd for C$_{13}$H$_{15}$N 185.1204, found 185.1204.

Compounds 1 and 2

The racemic mixture VI was converted to diastereomeric salts by adding one equivalent of L-(+)-tartaric acid. The crystals obtained by repeated fractional crystallization (10×) of the salt from methanol at room temperature were dissolved in H$_2$O. The solution was basified with 5N NaOH and extracted with methylene chloride. Evaporation of the extract gave analogue 1 as white crystals. The mother liquor of the fractional crystallization was converted back to free amine, through the same procedure as the crystals of compound 1, and converted to another pair of diastereomers by adding 1 equivalent of D-(−)-tartaric acid. This time the crystals of fractional crystallization from methanol afforded compound 2 as white crystals. The optical purity of compound 1 and 2 was checked by $^1$H-NMR analysis of their S-(−)-MTPA [α-methoxy-α-(trifluoromethyl)-phenylacetyl] amide derivatives. 12 mg (0.0475 mmol) of S-(−)-MTPA chloride in 50 μl of $CH_2Cl_2$ was added slowly to an ice cold solution of 5 mg (0.027 mmol) of compound 1 or 2 or the racemic mixture VI in 100 μl of $CH_2Cl_2$ containing 3.8 μl of $eT_3N$. The mixture was stirred at 0°–5° C. for 2 h. The reaction mixture was washed with 5% HCl, and extracted with $CH_2Cl_2$. Evaporation of the extract gave the crude amide derivatives. $^1$H-NMR ($CDCl_3$, 500 MHz) analysis of the amide derivatives of analogue 1 and 2 showed a single nitrogen proton peak at δ 6.83 and δ 6.72, respectively, while that of the amide derivative of the racemic mixture of amines showed two nitrogen proton peaks at δ 6.83 and δ 6.72.

Compound 1: white crystals: $[α]_D^{25} = +194.63°$ (c=6.7×10$^{-3}$, $CHCl_3$)

Compound 2: white crystals: $[α]_D^{25} = -192.16°$ (c=7.4×10$^{-3}$, $CHCl_3$)

Compounds 3 and 4

A solution of 150 mg (0.81 mmol) of compound 1 or 2 in 5.6 mL of dry ethanol was stirred with 3.8 mg of $PtO_2$ under hydrogen (1 atm) at room temperature for 1 h. Filtration and evaporation gave the compound 3 or 4 in quantitative yield.

$R_f$=0.34 (40% EtOAc in hexane, silica TLC saturated with $NH_3$);

IR ($CHCl_3$) ν 3358, 3281, 3013, 2917, 2847, 1595, 1468, 1451, 1437, 747, 718 cm$^{-1}$;

$^1$H NMR ($CDCl_3$, 300 MHz) δ 7.35–7.16 (4H, m), 2.94 (1H, dd, $J_1$=7.1 Hz, $J_2$=15.5 Hz) 2.65 (1H, dd, $J_1$=7.7 Hz, $J_2$=15.5 Hz), 2.21–2.08 (1H, m), 1.94–1.30 (10H, m);

$^{13}$C NMR ($CDCl_3$, 125.76 MHz) δ 151.35, 141.67, 126.92, 126.49, 125.46, 121.43, 61.73, 48.72, 35.778, 34.77, 26.42, 22.46, 21.96;

MS (70 eV), m/z 187 (M$^+$), 144, 130, 115, 91, 77; HRMS calcd. for $C_{13}H_{17}N$ 187.1355, found 187.1355.

Compound 3: colorless oil: $[α]_D^{25} = +24.12°$ (c=6.8×10$^{-3}$, $CHCl_3$).

Compound 4: colorless oil.

Compounds 5 and 6

To an ice cold solution of 281.3 mg (1.52 mmol) of analogue 1 or 2 in 1.76 mL of CH was added slowly 169 μL (1.79 mmol) of acetic anhydride. The mixture was stirred at room temperature for 7 h and then washed with 5% HCl and saturated aqueous $NaHCO_3$, respectively. After drying of the organic phase and removal of the solvent, the crude amide in 3.36 mL of dry THF was added to 342.8 mg (8.58 mmol) of $LiAlH_4$ (95%) in 16.8 mL of dry ethyl ether. The mixture was refluxed for 6h. Water 400 μM was then added slowly to this mixture at 0° C. The mixture was stirred for an additional 15 minutes and sufficient 2N NaOH was added to the mixture to dissolve the aluminum hydroxide. $CH_2Cl_2$ extraction and evaporation gave 287.7 mg (89%) of compound 5 or 6.

$R_f$=0.38 (20% EtOAc in hexane, silica TLC saturated with $NH_3$);

IR ($CHCl_3$) ν 3325, 3069, 3019, 2955, 2905, 2828, 2677, 1642, 1452, 1445, 1429, 745, 721, 650 cm$^{-1}$;

$^1$H NMR ($CDCl_3$, 500 MHz) δ 7.26–7.12 (4H, m), 5.80–5.72 (2H, m), 2.98 (1H, dd, $J_1$=7.3 Hz, $J_2$=14.9 Hz), 2.74–2.65 (1H, m), 2.64–2.54 (2H, m), 2.44–2.34 (2H, m), 2.30–2.06 (3H, m), 1.30 (1H, br, s) 1.08 (3H, t, J=7.1 Hz);

$^{13}$C NMR ($CDCl_3$, 125.76 MHz) δ 149.92, 141.98, 126.70, 126.14, 125.71, 125.56, 125.20, 121.86, 65.40, 40.02, 37.02, 36.75, 36.01, 26.33, 16.25;

MS (70 eV), m/z 213 (M$^+$), 198, 184, 180, 159, 144, 131, 115;

HRMS calcd for $C_{15}H_{19}N$ 213.1517, found 213.1517;

Compound 5: colorless oil: $[α]_D^{25} = +118.65°$ (c=6.65×10$^{-3}$, $CHCl_3$).

Compound 6: colorless oil.

Compound 7 and 8

A solution of 120 mg (0.563 mmol) of compound 5 or 6 in 4.0 mL of dry ethanol was stirred with 2.7 mg of $PtO_2$ under hydrogen (1 atm) at room temperature for 75 min. Filtration and evaporation gave the compound 7 or 8 in quantitative yield.

$R_f$=0.23 (20% EtOAc in hexane, silica TLC saturated with $NH_3$);

IR ($CHCl_3$) ν 3316, 2917, 2849, 1439, 1188, 1130, 746, 718 cm$^{-1}$;

$^1$H NMR ($CDCl_3$, 300 MHz) δ 7.30–7.10 (4H, m), 2.97 (1H, dd, $J_1$=7.0 Hz, $J_2$=15.5 Hz), 2.60 (1H, dd, $J_1$=15.5 Hz), 2.52–2.35 (3H, m), 1.93–1.80 (1H, m), 1.79–1.67 (1H, m), 1.67–1.15 (7H, m), 1.03 (3H, t, J=7.1 Hz);

$^{13}$C NMR ($CDCl_3$, 125.76 MHz) δ 147.25, 142.77, 127.10, 125.89, 122.69, 66.76, 42.92, 36.94, 35.37, 33.63, 27.34, 22.60, 21.79, 15.79;

MS (70 eV), m/z 215 (M$^+$), 172, 158, 141, 129, 115, 91;

HRMS calcd for $C_{15}H_{21}N$ 215.1674, found 215.1674;

Compound 7: colorless oil; $[α]_D^{25} = -3.53°$ (c=6.8×10$^{-3}$, $CHCl_3$);

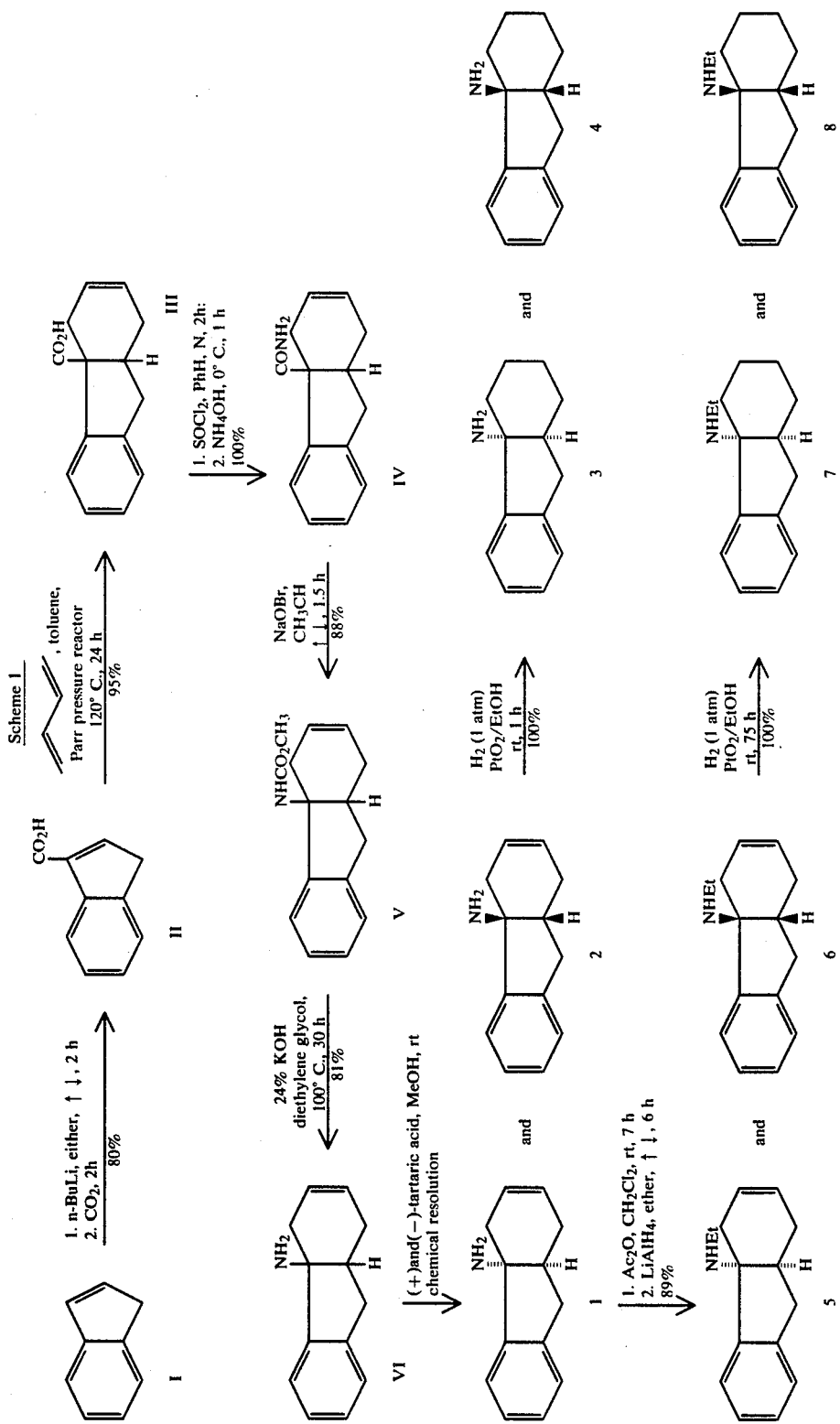

EXAMPLE II

Synthesis of $X_1/X_2$ Substituted Fluorenamines

This example describes the synthesis of the compounds represented by general formula I wherein $X_1$ and $X_2$ can be substituted with substituents other than hydrogen. Also, it should be noted that the numerals following the named compounds in EXAMPLE II correspond to the numbered compounds of Scheme 2.

These synthetic schemes are identical to that employed in the preparation of compounds 1-8 of EXAMPLE I, with the exception that one must use an appropriately substituted indene-3-carboxylic acid I in place of indene-3-carboxylic acid. After the chemical resolution step, the primary amine VI can be directly alkylated with an alkyl halide or sulfate ($R^1X$) to provide a secondary amine [$-NH(R^1)$]. The alkylation can also be carried out in a stepwise fashion by first acylating the amine with a carboxylic acid halide or anhydride followed by reducing the carbonyl group of the amide with a hydride reagent such as lithium aluminum hydride. A reductive alkylation procedure may also be used to introduce $R^1$ by first reacting the amine with an aldehyde or ketone, and then reducing the resulting imine using sodium cyanoborohydride, hydrogen, lithium aluminum hydride, etc.

The alkylation step can be repeated a second time in a fashion identical to the above to convert the secondary amine to a tertiary amine [i.e., $-N(R^1)(R^2)$]. In the case where a dihalide or disulfate is employed (i.e., $X(CH_2)_nX, n=4$ or 5) in the alkylation of the primary amine, the amino group can be transformed to the cyclic piperidino or pyrrolidino group.

In the case where $X_1$ or $X_2$ is methoxy group, such group can be cleaved with trimethylsilyl iodine to provide the hydroxy compound IX, or treated with hydrogen and a metal catalyst to afford the saturated structure VII. The hydroxy compound IX can also be saturated with hydrogen gas and a metal catalyst to provide X.

To prepare the analogues with $X_1$ and/or $X_2 = NH_2$, the nitro substituted indene-3-carboxylic acid can be used, for the nitro group can be transformed to an amino group at or near the end of the synthesis by standard reduction procedures (e.g., Fe, $H^+$, or $H_2$/metal catalyst).

In the case where $X_1$ and/or $X_2 = NH_2$, the amino group can be transformed to isothiocyanate ($N=C=S$) by reaction with thiophosgene and a base. Prior protection of the other amino group will be required in the case where $R^1$ and $R^2=H$, and the use of the trifluoroacetyl group is preferred for this purpose.

In the case where $X_1$ and/or $X_2 = SH$, care must be taken in the hydrogenation step to avoid loss of sulfur, and therefore the use of diimide is preferred in the conversion of VII to VIII.

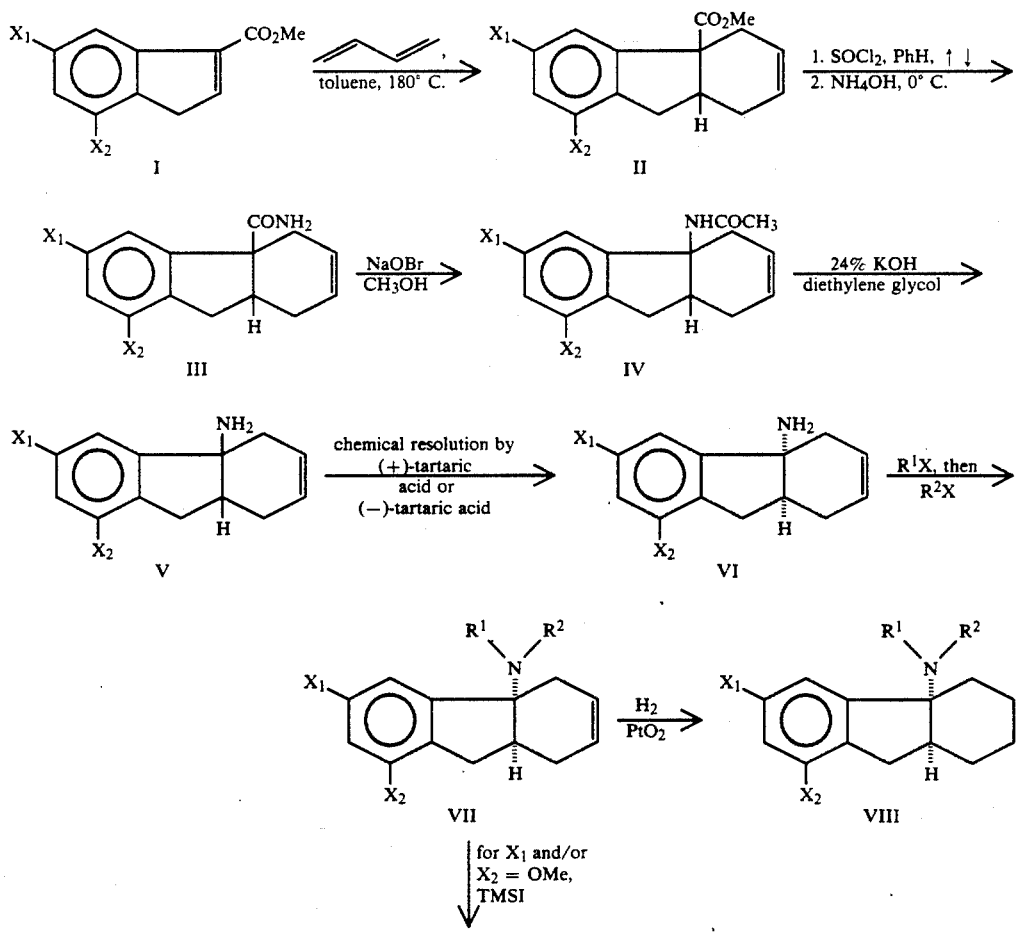

-continued

Scheme 2

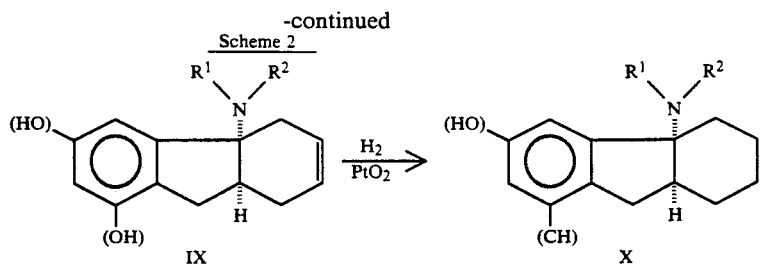

EXAMPLE III

Radioligand Binding Assay

Radioligand binding studies were carried out in accord with the published protocol of I. J. Reynolds, et al., $^3$H-labeled MK-801 binding to the excitatory amino acid receptor complex from rat brain is enhanced by glycine, Proc. Acad. Sci. USA, 84, 7744–7748 (1987) to evaluate the in vitro affinities of the newly synthesized compounds for the PCP binding sites of the NMDA receptor complex.

Well washed rat brain homogenate suspensions in 1.0 mL of 10 mM Hepes (pH =7.4 at room temperature) that contained 0.3–0.6 mg of protein, 0.5–1 nM (+)-[$^3$H]MK-801, 100 μM glutamate, 30 μM glycine, and varying concentrations of the compounds 1–8 of EXAMPLE I as appropriate or 30 μM (+)-MK-801 for nonspecific binding were incubated at room temperature for 2 hours and then terminated by filtration under vacuum using a 24-well cell harvester (Brandel, Gaithersburg, Md.) over glass fiber filters (No. 32, Schleicher & Gaithersburg, Inc., Keene, N.H.). Filters were washed with two 5 mL aliquots of assay buffer. Radioactivity trapped on filters was measured by liquid scintillation spectrometry using a Beckman LS 1801 scintillation counter at 50% efficiency.

The relative potencies of the compounds 1–8 of EXAMPLE I in displacing bound (+)-[$^3$H]MK-801 and their IC$_{50}$'s are shown in TABLE 1.

TABLE 1

Relative potencies of PCP analogues in displacing (+)-[$^3$H]MK-801 bound to rat brain homogenates.

| Agent | IC$_{50}$ (nM) | Relative Potency (%) |
|---|---|---|
| PCP | 35 ± 1 | 100 |
| TCP | 11 ± 1 | 318 |
| 1 | 114 ± 14 | 31 |
| 2 | 2241 ± 135 | 2 |
| 3 | 19 ± 1 | 184 |
| 4 | 1391 ± 49 | 3 |
| 5 | 224 ± 5 | 16 |
| 6 | 676 ± 16 | 5 |
| 7 | 68 ± 7 | 51 |
| 8 | 546 ± 40 | 6 |

Data in the table represent the means of three experiments, each carried out in duplicate that varied less than 10%, and are reported ±SEM.

The following points are noteworthy regarding structure versus activity: (1) All the enantiomers of R stereochemistry at the amine bearing carbon atom (i.e. compounds 1,3,5 and 7) were more potent in binding than the corresponding enantiomers of S stereochemistry at the amine bearing carbon atom, which are not within the scope of the subject invention, i.e. compounds 2, 4, 6 and 8. Assigning PCP a relative potency of 100%, such S enantiomers ranged in potency from 2 to 6% while the such R enantiomers ranged in potency from 16 to 184%. Clearly, such R enantiomers show higher affinity for the PCP binding sites, and as a consequence minor structural variations give rise to a broader spread of binding potency than found with the series of such S enantiomers; (2) Compound 3 shows an affinity of IC$_{50}$= 19 nM and is more potent in binding than PCP; (3) The 73 fold binding difference found between the enantiomeric pair of compounds 3 and 4 is larger than the difference found previously for any such pairs of PCP-like compounds possessing higher binding affinities than PCP itself. This result further strengthens claims of the stereoselective nature of the PCP/MK-801 binding sites.

What is claimed is:

1. A compound represented by formula I:

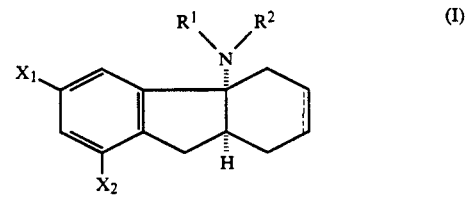

wherein:
X$_1$ is selected from the group consisting of [H,] OH, NH$_2$, SH, N=C=S and OCH$_3$;
X$_2$ is selected from the group consisting of H, OH, NH$_2$, SH, N=C=S and OCH$_3$;
R$^1$ is selected from the group consisting of H and a C$_1$-C$_4$ linear or branched alkyl group;
R$^2$ is selected from the group consisting of H and a C$_1$ -C$_4$ linear or branched alkyl group;
or R$^1$ and R$^2$ can be joined to form a pyrrolidine ring or a piperidine ring;
⸺ represents a saturated or unsaturated bond; or pharmaceutically acceptable salts thereof;
with the proviso that:
(1) said compound is in the cis-fused form; and
(2) said compound is in the enantiomer of R stereochemistry at the amine bearing carbon atom substantially free of any other stereoisomer.

2. A composition comprising a therapeutically effective amount of a compound of claim 1 and a pharmaceutically acceptable carrier.

3. A method for treating or preventing neuronal cell loss, treating neurodegenerative diseases or ameliorating the neurotoxic effect induced by excitatory amino acids interacting with the NMDA receptor of a nerve cell which comprises administering to a mammal a therapeutically effective amount of a compound of claim 1.

4. The method of claim 3 wherein said mammal is a human.

5. The method of claim 3 wherein said neuronal cell loss is associated with stroke, ischemia, CNS trauma, hypoxia or hypoglycemia.

6. The method of claim 3 wherein said neurodegenerative disease is selected from the group consisting of Alzheimer's disease, amytrophic lateral sclerosis, Huntington's disease and Down's syndrome.

7. The method of claim 3 wherein said neurotoxic effect induced by excitatory amino acids interacting with the NMDA receptor of a nerve cell is caused by ischemic brain insults.

8. A method for blocking ion fluxes through the NMDA receptor-associated ion channel in a mammal which comprises administering to said mammal an effective amount of a compound of claim 1.

9. A compound represented by formula I:

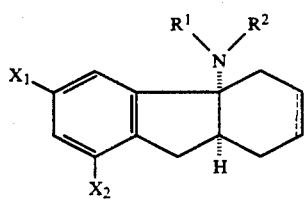

wherein:
- $X_1$ is selected from the group consisting of H, OH, $NH_2$, SH, N=C=S and $OCH_3$;
- $X_2$ is selected from the group consisting of OH, $NH_2$, SH, N=C=S and $OCH_3$;
- $R^1$ is selected from the group consisting of H and a $C_1$-$C_4$ linear or branched alkyl group;
- $R^2$ is selected from the group consisting of H and a $C_1$-$C_4$ linear or branched alkyl group;
- or $R^1$ and $R^2$ can be joined to form a pyrrolidine ring or a piperidine ring;
- ═ represents a saturated or unsaturated bond; or pharmaceutically acceptable salts thereof;

with the proviso that:
(1) said compound is in the cis-fused form; and
(2) said compound is in the enantiomer of R stereochemistry at the amine bearing carbon atom substantially free of any other stereoisomer.

10. A composition comprising a therapeutically acceptable amount of a compound of claim 9 and a pharmaceutically acceptable carrier.

11. A method for treating or preventing neuronal cell loss, treating neurodegenerative diseases or ameliorating the neurotoxic effect induced by excitatory amino acids interacting with the NMDA receptor of a nerve cell which comprises administering to a mammal a therapeutically effective amount of a compound of claim 9.

12. The method of claim 11 wherein said mammal is a human.

13. The method of claim 11 wherein said neuronal cell loss is associated with stroke, ischemia, CNS trauma, hypoxia or hypoglycemia.

14. The method of claim 11 wherein said neurodegenerative disease is selected from the group consisting of Alzheimer's disease, amyotrophic lateral sclerosis, Huntington's disease and Down's syndrome.

15. The method of claim 11 wherein said neurotoxic effect induced by excitatory amino acids interacting with the NMDA receptor of a nerve cell is caused by ischemic brain insults.

16. A method for blocking ion fluxes through the NMDA receptor-associated ion channel in a mammal which comprises administering to said mammal an effective amount of a compound of claim 9.

* * * * *